United States Patent
Wundrich et al.

(10) Patent No.: US 9,808,641 B2
(45) Date of Patent: Nov. 7, 2017

(54) SYSTEM AND METHOD FOR NON-INVASIVE NEURONAL STIMULATION

(71) Applicant: EBS TECHNOLOGIES GMBH, Kleinmachnow (DE)

(72) Inventors: Ingo Wundrich, Kleinmachnow (DE); Udo Warschewske, Berlin (DE)

(73) Assignee: EBS TECHNOLOGIES GMBH, Kleinmachnow (DE)

( * ) Notice: Subject to any disclaimer, the term of this patent is extended or adjusted under 35 U.S.C. 154(b) by 0 days.

(21) Appl. No.: 14/916,011

(22) PCT Filed: Sep. 5, 2014

(86) PCT No.: PCT/EP2014/068945
§ 371 (c)(1),
(2) Date: Mar. 2, 2016

(87) PCT Pub. No.: WO2015/032898
PCT Pub. Date: Mar. 12, 2015

(65) Prior Publication Data
US 2016/0199662 A1    Jul. 14, 2016

(30) Foreign Application Priority Data

Sep. 6, 2013   (DE) .................... 10 2013 014 875
May 23, 2014   (DE) .................... 10 2014 007 645
Aug. 11, 2014  (DE) .................... 10 2014 011 867

(51) Int. Cl.
| A61N 1/00 | (2006.01) |
| A61N 2/00 | (2006.01) |
| A61N 1/04 | (2006.01) |
| A61N 1/36 | (2006.01) |
| A61N 2/02 | (2006.01) |
| A61N 1/32 | (2006.01) |

(52) U.S. Cl.
CPC .......... *A61N 2/002* (2013.01); *A61N 1/0456* (2013.01); *A61N 1/0484* (2013.01); *A61N 1/36014* (2013.01); *A61N 1/36025* (2013.01); *A61N 1/36046* (2013.01); *A61N 1/36103* (2013.01); *A61N 2/006* (2013.01); *A61N 2/02* (2013.01); *A61N 1/323* (2013.01)

(58) Field of Classification Search
CPC .... A61N 2/002; A61N 1/0456; A61N 1/0526; A61N 1/36014; A61N 1/36025; A61N 1/36046; A61N 1/36103; A61N 2/006; A61N 1/323
USPC .......................................................... 600/3
See application file for complete search history.

(56) References Cited

U.S. PATENT DOCUMENTS

| 8,475,506 B1* | 7/2013 | Bendett ............... A61N 5/0622 607/88 |
| 8,948,875 B2 | 2/2015 | Paulus et al. .................. 607/45 |
| 2004/0131998 A1 | 7/2004 | Marom et al. ................ 434/236 |
| 2011/0144716 A1* | 6/2011 | Bikson ................. A61N 1/0529 607/45 |
| 2012/0059438 A1* | 3/2012 | De Ridder ......... A61N 1/36075 607/70 |

FOREIGN PATENT DOCUMENTS

| CN | 101 491 715 | 7/2009 | .............. A61N 1/18 |
| DE | 10 2011 120 213 | 6/2012 | .............. A61N 1/36 |
| WO | WO 2012/000546 | 1/2012 | .......... A61B 5/0482 |
| WO | WO 2012/089588 | 7/2012 | .............. A61N 1/36 |

OTHER PUBLICATIONS

Sabel, et al., "*Non-Invasive Alternating Current Stimulation Improves Vision in Optic Neuropathy*", Restorative Neurology and Neuroscience, Jan. 1, 2011 (Jan. 1, 2011), pp. 493-505, XP055153090, Netherlands, DOI 10.3233/RNN-2011-0624, Retrieved from the Internet: URL: http://www.ncbi.nlm.nih.gov/pubmed/22124039, the whole document. (last accessed on Jun. 13, 2016).
The Notification Concerning the Transmittal of International Preliminary Report on Patentability (Chapter I of the Patent Cooperation Treaty), in English, dated Mar. 17, 2016, the International Preliminary Report on Patentability (Chapter I of the Patent Cooperation Treaty), in English, dated Mar. 8, 2016, the Written Opinion of the International Searching Authority, in English (dated Mar. 8, 2016—mailed with the English translation of the International Preliminary Report on Patentability), and the International Search Report, in English, dated Nov. 28, 2014, which were issued by the International Bureau of WIPO in Applicant's corresponding international PCT application having Serial No. PCT/EP2014/068945, filed on Sep. 5, 2014.

\* cited by examiner

*Primary Examiner* — Robert N Wieland
(74) *Attorney, Agent, or Firm* — Bodner & O'Rourke, LLP; Gerald T. Bodner; Christian P. Bodner

(57) ABSTRACT

The invention relates to a system for electrical and/or magnetic neuronal stimulation, comprising a signal generator for generating a stimulation signal, in particular an alternating-current stimulation signal, an applicator for applying the stimulation signal, in particular in an area on or directly around the optic nerve, a lead for deriving a measurement signal, in particular an EEG signal, a biomarker calculation unit for calculating a biomarker based on the measurement signal, and an optimization unit, in particular for performing a stochastic optimization process, for optimizing the value of the biomarker by varying the stimulation signal.

44 Claims, No Drawings

SYSTEM AND METHOD FOR NON-INVASIVE NEURONAL STIMULATION

The invention relates to a system and a method for noninvasive electrical and/or magnetic stimulation, in particular for neuronal stimulation of a patient.

Presently, essentially two fundamental methods for electrical brain stimulation are to be differentiated according to the prior art, specifically invasive and noninvasive electrical brain stimulation.

In clinical neurology, methods for brain stimulation are increasingly gaining significance as a promising supplement to conventional surgical or pharmacological intervention measures. This firstly relates to the well-established invasive methods for deep brain stimulation via implanted "brain pacemakers", which are presently used above all for the effective treatment of movement disorders (for example, in the case of Parkinson, essentially tremors and dystonia), but has also been studied for the treatment of numerous other neurological disorders.

In addition, noteworthy treatment successes have been achieved in recent years in the treatment of neurological damage by way of the targeted use of noninvasive, magnetic or electrical, transcranial stimulation methods, which are apparently capable of effectively assisting the regeneration of fundamental neuronal plasticity.

One of the quantitatively most important causes of brain damage is found in the indication of stroke. Approximately 200,000 strokes take place each year in Germany alone. Approximately 65,000 cases of death are associated with this, which makes stroke the third most frequent cause of death in Germany. The predominant part of the survivors are affected by severe neurologically-related impairments; this relates above all to the motor functions (appearances of paralysis), speech function, and vision function (for example, restrictions of the field of vision).

While the focal point of the currently typical rehabilitation measures is in reestablishing or improving the motor and speech proficiencies, to keep the patients at least out of permanent need for care, rehabilitation measures are hardly available for improving the visual proficiencies, which are frequently strongly impaired.

Spontaneous self-healing as a result of neuroplastic processes has very different individual courses, at the same time, the described sensory restrictions are linked to a high level of psychological stress for the affected patients. Because of these facts and against the background of the high number of patients, there is an extraordinarily large amount of interest in novel and effective treatment concepts, above all if they are noninvasive or have a low use-risk ratio. Electrical or magnetic, transcranial stimulation methods appear to be an approach of particular interest in this context.

The noninvasive methods in the field of electrical neurostimulation of brain areas are predominantly the so-called transcranial methods for noninvasive therapy of the brain. The therapeutic stimulation takes place in this case without an intervention engagement in the brain. Instead, the treatment is carried out "transcranially", i.e., from outside the skull "through the skull". Differentiation is made with respect to the applied current within the electrical stimulation methods between transcranial direct current stimulation (tDCS), transcranial stimulation with randomized high-frequency current signals (tRMS—transcranial high-frequency random noise stimulation), and transcranial alternating current stimulation (tACS). Provably lasting neuroplastic changes can be achieved using transcranial electrical brain stimulation, which are accompanied by elevated electrical activity in neuronal structures or the synchronization of the so-called CSTC control loops (cortical-striato-thalamo-cortical loop model). In the case of transcranial direct-current stimulation, it is presumed that the membrane potential of cortical neurons and the activity ("firing rate") of individual neurons can be modulated by the stimulation. If an elevated activity results, this corresponds to long-term potentiation, while reduced activity corresponds to long-term depression of the neuronal signal transmission. tRNS represents a complementary and newer method of noninvasive brain stimulation. In contrast to tDCS, tRNS does not include a direct current component and there is no indication that inhibitory aftereffects can be induced. In addition to potentially greater safety, a further advantage is seen in that depolarization of cells of any orientation takes place independently of the flow direction of the current. The effect is attributed to synaptic signal amplification, improved signal relay, and elevated neuronal activity by noise introduction according to the principle of "stochastic resonance".

While the probability of neuronal signal emission ("firing rate probability") can be modulated by means of tDCS and tRMS according to the present state of knowledge, transcranial alternating current stimulation (tACS) is a method which apparently can induce or influence specific oscillatory activities inside neuronal structures, which are associated with the excitability of pyramid cells and the synchronization of CSTC control loops. It is presumed in this case that the method interacts directly with brain state-specific oscillations (a brain state is understood in this context as a mental state which is accompanied by the synchronization of specific neuronal composites).

In transcranial electrical brain stimulation, two or more electrodes are placed on or below the scalp of the patient and a direct current or alternating current is applied thereto for a limited duration of up to 40 minutes for stimulation of the neuronal circuits in the brain.

In addition, a differentiation can be made between direct and indirect methods in the methods of brain stimulation. In the direct methods, cortical or subcortical structures of the brain are influenced directly by the applied stimulus, while in the indirect methods, the stimulation of the brain takes place indirectly via the stimulation of the brain nerves (for example, optical nerve, vagus nerve) or the stimulation of peripheral nerves.

Furthermore, a system for noninvasive electrostimulation is known from the prior art, which is based on the principle of rtACS. In this case, electrical brain stimulation is performed using alternating current not transcranially, but rather indirectly via the retina and the optical nerve (retinofugal stimulation). For this purpose, the electrodes are placed directly around the eyes. In the previous studies, the system was shown to be highly effective in the treatment of neurological vision disorders in a part of the patients (responders). The treatment is suitable not only for stroke patients, but rather also for other forms of vision disorders, which are to be attributed to neurological damage of the brain and the optic tract (for example, in the case of degenerative illnesses or traumatic damage of the brain). The potential of this treatment concept appears to be immense, however, the efficacy observed up to this point has been very different in individuals, accordingly, differentiation is made between "responders" and "nonresponders". According to the present state of neuroscience, it is to be presumed that a stimulation treatment optimized individually for the respective patients will result in very much better efficacy, whereby the condition for comprehensive use in neurorehabilitation would be provided. Because the fundamental mechanisms (similarly as in the other methods of electrical brain stimulation) are only inadequately understood, the optimization of the treatment methods has only progressed slowly.

It is therefore the object of the present invention to provide a system and a method for electrical and/or magnetic stimulation, in which the stimulation can be dynamically adapted to the patient and therefore optimized.

This object is achieved by a system according to claim 1 and a method according to claim 7. Advantageous embodiments are described in the dependent claims.

In particular, a system is provided, which comprises:
- a signal generator for generating a stimulation signal, in particular an alternating current stimulation signal,
- an application device for applying the stimulation signal, in particular in a region on or directly around the optic nerve,
- a derivation line for deriving a measurement signal, in particular an EEG signal,
- a biomarker calculation unit for calculating a biomarker based on the measurement signal,
- an optimization unit for updating the optimization criterion, i.e., for optimizing the value of the biomarker by variation of the stimulation signal.

Furthermore, a method is provided having the following steps:
- deriving a measurement signal, in particular an EEG signal,
- generating a stimulation signal, in particular an alternating current stimulation signal, wherein preferably the generated stimulation signal also comprises artificial noise,
- applying the stimulation signal by means of electrodes, i.e., electrical and/or magnetic stimulation, in particular in a region on or directly around the optic nerve, and
- varying the stimulation signal in dependence on a biomarker, which is determined from the measurement signal and/or conscious feedback of the patient, in particular in consideration of items of frequency, amplitude, phase, and/or location information of the measurement signal.

It is apparent that the measurement signal can comprise a plurality of individual signals, for example, originating from a plurality of EEG electrodes. The stimulation signal can also comprise a plurality of individual signals.

The magnetic stimulation can be performed on the basis of the known transcranial magnetic stimulation (TMS).

The biomarker in this context is an element from a feature space, which sufficiently describes the state of a patient, or especially his brain, with respect to a physical functionality or a clinical picture. Biomarkers can be either illness-related or therapy-related. An illness-related biomarker provides information about an illness which is imminent or already exists in a (very) early stage, while in contrast a therapy-related biomarker specifies whether and how the therapy acts on a specific patient, and how his organism will implement it. This differentiation is significant for setting goals in the optimization.

The biomarker can be one-dimensional or multidimensional. The feature dimensions can additionally be weighted. The weighting can relate to a set of statistical characteristic values. The optimization according to the invention can consist in this case of coming as close as possible to specific values, or a specific state, respectively. In some embodiments of the invention, this does not necessarily relate to reaching local or global extremes in this case.

In a further embodiment, it is important to avoid the approach to risk states in the space of the biomarker, whether by avoiding these ranges or ending or restarting the therapy in the event of hopeless approach.

In a further embodiment, during the therapy, i.e., the optimization of the biomarker, the patient receives instructions from the system, for example, written or acoustic, according to the present biomarker. One goal of such instructions is, for example, a change of the attention state of the patient. Measurement data specific to the attention state are thus generated, for example, which can be relevant for the biomarker. In this case, a separate biomarker space results for each attention state, which can be imaged in another by learned images.

The attention states of the brain can reach from sleep or relaxation up to high levels of concentration when solving difficult problems. This also includes predefined movement sequences, for example, to assist the transcranial stimulation of the motor cortex.

Any approximation to a target state or ideal state is referred to hereafter as optimization. The practical implementation can be performed, for example, by optimization in the meaning of an extreme value determination of a distance function between target values and measured biomarker values.

The existence of a significant metric is decisive for the structure of the space in which the optimization is to be performed, i.e., the topology of biomarkers related to the state of the patient or the course of the therapy.

The application devices can be, for example, electrodes for electrical stimulation and/or coils for magnetic stimulation.

According to the invention, superposition of direct current and alternating current signals with artificial noise, in particular with white and filtered noise, can be performed.

In a further embodiment of the invention, alternating current signals are overlaid by noise, which can be provided over the entire applicable time axis or in windows as bursts.

In a further embodiment, free of the classification scheme "direct current/alternating current/noise", amplitude-restricted signals in general can be applied with sampling rates up to, for example, 10 MHz during a therapy.

In a further embodiment of the invention, the therapy does not take place as regulation of biomarkers, i.e., adaptively, but rather follows a plan previously optimized in a diagnosis/planning phase The system and method according to the invention enable the stimulation to be adapted during the stimulation procedure, to achieve maximum response. By way of the automatic acquisition of the measurement signal and the determination of the biomarker simultaneously or with minimal time delay to the stimulation, the stimulation signal can be varied within a short time so that a non-responder (in relation to a first stimulation signal) becomes a responder (in relation to the varied stimulation signal).

A patient-individual automatic optimization of the electrostimulation during the treatment is therefore enabled, in that a previously developed biomarker, which is relevant for the plasticity assistance, is observed and is maximized via an adaptation of the stimulation, for example, via a variation of the stimulation parameters. A strong increase of the proportion of the responders or super responders can therefore be achieved and finally a strongly improved noninvasive electrostimulation method can be provided for effective treatment of neurological disorders, in particular vision disorders, which sets completely new standards, inter glia, in the rehabilitation of stroke patients.

The optimization criterion is based on the differentiation between illness-related and therapy-related biomarkers. In the first case, there is a standard region in the biomarker space for healthy humans, the achievement of which promises healing. The goal is to reach this standard region or to come as close as possible to it with respect to a significant metric. In the case of therapy-related biomarkers, target regions in the biomarker space are also conceivable, which are accompanied by particularly good response of the patient to the therapy. In this case, the therapy-related biomarker can be used in principle as a selection criterion for the applicability of the therapy and therefore can provide indications of possible success. On the other hand, it is possible in preparation with additional therapeutic (for example, pharmacological) measures to bring the patient into a more favorable general state for the therapy, i.e., to move the biomarker closer to a target region.

In a corresponding embodiment, target regions are made assessable by a scale, the criteria of which take into consideration, for example, the therapeutic success, the response of the patient to the therapy, or the probability of reaching them.

The solution approach takes into consideration the fact that mechanical foundations of reestablishing neurological breakdowns and the assistance thereof by means of transcranial stimulation methods are only inadequately understood and is therefore based on the most extensive possible data-driven procedure.

For a simultaneous location-specific, frequency-specific, and phase-specific derivation and stimulation, an electrode cap having freely programmable derivation and stimulation electrodes can be used. The freedom of form required for this purpose can additionally be improved by the use of conductive textiles.

According to the invention, a regulated stimulation system is therefore provided, which drives the stimulation paradigm on the basis of the present state parameter of the patient independently by changing stimulation characteristic values in a targeted manner in the direction of an optimum brain state and therefore adapts the therapy individually to the patient, improves the efficacy thereof, and/or strongly increases the relative proportion of responders or super responders.

The stimulation can be performed in this case, depending on the embodiment, not only as retinofugal stimulation, but rather, by means of a flexible configuration of the electrodes on the head, also as transcranial electrostimulation, for example, in the region of the visual cortex.

In one embodiment of the invention, it is provided that the system has a noise generator for generating artificial noise. The possibility can therefore be provided, in addition to the use of discrete frequencies within specific frequency intervals, of also coupling noise components into the stimulation, to additionally use the influence of noise in neuronal plasticity, which is well-established in current science.

In general, the biomarker is a set of weighted parameters, which have properties or features which are characteristic with respect to the diagnosis and/or the therapy goal for all data sets, which are obtained by the analysis of the measurement signal in consideration of various signal properties (for example, items of amplitude, frequency, phase, and/or location information of the measurement signal and/or more complex imaging of the signals, for example, cross-correlations, wavelet coefficients, or clinically assessable test statistics).

In a further embodiment of the invention, it is provided that the functional dependence of the biomarker was determined by machine learning from training data, in particular the biomarker is a function of items of amplitude, frequency, phase, and/or location information of the measurement signal or the functional images thereof. The weighting parameters can also be determined by machine learning from training data. One embodiment of such a learning method is that the measurement data for the determination of the biomarker are segmented on the basis of specific criteria. This can be performed both on the basis of chronological criteria (for example, point in time before and after a therapy attempt) and also on the basis of qualitative criteria for evaluating the therapy attempt (thus, for example, on the basis of quantifiable features, for example, size of the field of vision, visual acuity, color and contour vision). Trends and correlations of characteristic features of the measurement signals may be ascertained within the segments. Significance and scattering of the features found can be used, for example, for weighting the feature parameters.

Since the functional relationships between the measurement signal and an informative biomarker can be complex, nonlinear relationships and, for example, the EEG measurement signals can be very high-dimensional data overall, advanced learning methods, for example, support vector machines (SVMs) can be used here in particular.

In this case, a biomarker space of its topological conditions can be viewed, for example, as a linear scalar product space in consideration of the significance of its dimensions (additionally the definition of the metric) or as a nonlinear diversity. The latter can be mapped using methods of nonlinear dimensionality reduction, for example, isomap or local linear embedding.

In a further embodiment of the invention, the biomarker spaces for a specific patient population are not permanently installed in the device, but rather are learned from the therapy courses in the set of all patients who are treated using the device. This would be possible, for example, by communication via a network of computers in connected therapy centers.

In a further embodiment of the invention, the stimulation therapy is pharmacologically assisted. The medication can be predefined or can result from the course of therapy or the optimization of the biomarker. An implementation path can be produced, for example, via an interface to infusion devices.

The biomarker may be determined in real-time or with minimal time delay from the measurement signal. Therefore, in this embodiment of the invention, a response of the biomarker can be established practically without delay, and therefore an adaptation of the stimulation signal can also optionally take place immediately.

In a further embodiment of the invention, it is provided that the stimulation signal is generated by a programmable functional generator, which is preferably implemented in a field programmable gate array (FPGA).

In this embodiment, the core of the stimulation system is an FPGA, via which one current source can be controlled separately per channel. It can be provided in this case that the output is defined via one or more digital tables, which are combined with one another (for example, 8000 entries at 16 bits per table), which are read out at a sampling rate between 100 Hz and 1 MHz.

In this case, 12 or 14 bits are sufficient for the coding of the amplitude, so that the remaining 4 or 2 bits, respectively, can be interpreted as commands within the stimulation table ("wave table"). Such commands can be: end of waveform, switch table (read out the values from a further table); ground (switch the channel to ground—therefore, in the case of multiple channels, not only the current strength but rather also the current flow direction can be influenced: "steering"); day (transmit a TTL signal/timestamp, which is recorded by the EEG amplifier), repeat until (repeatedly read out the table until a specific state has occurred). The functional behavior of the stimulator can be synchronized with stimulation paradigms in this manner.

Optimization of the table loading cycles can be performed by additional modulation/scaling of existing tables with respect to the amplitude or sampling rate thereof or by superimposing multiple tables. In a further embodiment of the invention, such changes of the curve forms can be carried out during the execution of a current table. Thus, for example, using a command: scale amplitude/scale sampling rate (amplitude or sampling rate, respectively, is resealed), the amplitude or the frequency behavior of the stimulation paradigm is modulated at a previously determined point of the stimulation sequence (for example, during a zero crossing of the signal) using a value which was previously stored in a register of the stimulator (i.e., asynchronous control of the stimulator). This is similarly possible in a further embodiment of the invention using pauses or interruptions, for example, by way of a command such as scale delay (number of blank samples of a table), whereby a phase modulation of the stimulation signal is possible, for example, with respect to a neuronal measurement signal.

Various curve forms can be stored as possible stimulation signals in the programmable function generator. The optimization unit can therefore switch between various stimulation signals and, in a large parameter space, select the optimum settings for the stimulation or the stimulation signals are generated and applied in a nonparametric manner.

In a further embodiment of the invention, an expansion is provided using a device for generating physiological stimuli (for example, generating discrete light stimuli in different sectors of the field of vision) and/or a feedback input device (for example, a manual switch, touch screen, or rotary knob), wherein the device for generating physiological stimuli is preferably synchronized with the measurement device and the feedback data of the feedback input device are preferably taken into consideration in the calculation of the biomarker.

It can be provided in this case that the biomarker, and therefore in dependence on the biomarker also the stimulation signal, is established in dependence on feedback data, which the patient inputs via a feedback input device.

In a further embodiment of the invention, acoustic stimuli are applied, for example, via headphones, for stimulation of auditorily-relevant and higher-level brain areas.

In a further embodiment of the invention, more complex optical/visual stimuli (for example, lattice or checkerboard patterns) are combined with an above-mentioned feedback input device, to evaluate the functionality of higher-level visual processing in the given patients and have it incorporated into the optimization of the biomarker. This functionality comprises, for example, spatial resolution (frequency and modulation depth), orientation of patterns, movement, spatial vision.

In a further embodiment of the invention, stimuli of the mentioned type are used both for therapeutic purposes and also for updating the biomarker by measuring corresponding evoked potentials.

In some embodiments, the stimulation signal of a single or multiple electrodes has only direct current, alternating current, or high-frequency noise. In other embodiments, superpositions of all three of the possible current paradigms are applied at one or more electrodes.

In a further embodiment of the invention, it is provided that the functional dependence of the biomarker on the measurement signal is determined by machine learning using training data from test subjects, in particular by supervised clustering using support vector machines, additionally assisted by databases. The method can therefore "learn" from the data pool of all patients and each newly added patient.

In this embodiment of the invention, a relevant EEG biomarker set—a so-called "EEG fingerprint of the recovery of the visual system"—can be derived from existing test subject data (responder and nonresponder) with the aid of pattern recognition methods (supervised clustering using support vector machines), which takes into consideration the various features of the measurement signal (for example, items of frequency, phase, and location information). The assignment of the test subject data to responders and nonresponders can be performed manually, for example, by an experienced physician.

Based on this observed "EEG fingerprint", particularly effective algorithms for rapid stochastic optimization of the stimulation parameters can then be used.

In a further embodiment of the invention, not only are EEG features imaged in the biomarker space, but rather also further measurements, for example, ECG or functional magnetic resonance tomography, or conscious patient feedback (see below). This includes diagnostic tests such as perimetry or audiometry.

In a further embodiment of the invention, it is provided that during the stimulation method, an optimization method, in particular a stochastic optimization method, is carried out to maximize the biomarker by way of a variation of parameters of the stimulation signal.

Stochastic optimization methods have proven to be particularly robust in relation to local minima in experiments in which, depending on the embodiment, a very high number of parameters to be varied of the stimulation signal is provided.

According to the invention, various stochastic optimization methods of different classes (for example, evolution strategies, genetic algorithms, stochastic gradient descent) can be used, the shared feature of which is that changes can be performed on the manipulated variables and evaluated post hoc, as to whether they have resulted in an improvement. Methods of active learning are also applicable in this case, which are directed to maximum partitioning of the remaining search space, and methods of reinforcement learning ("reward principle").

In this case, the fact is taken into consideration that the operations required for optimization cannot be planned exactly beforehand, but rather the planning relates to trajectories in the biomarker space or to biomarker spaces linked to one another by images. These trajectories are planned on the basis of profiles, which require the least possible interaction from the patient, for example, manage with the smallest possible amount of energy (pain reduction), or particularly minimize specific risks (in dependence on additional illnesses, which are not the subject of the therapy, for example, epilepsy).

The optimization is ended when, for example, the edge of a target region in the biomarker space is reached, the centroid of a target region in the biomarker space is reached, a further optimization in the planned direction appears impossible, or the biomarker cannot leave the entry region of a risk region. The set of the risk regions is a set of coherent sets in which the biomarker relates to disadvantageous effects on the patient. This is the case, for example, with influence of functions such as heartbeat or inducing fear states.

In a further embodiment of the invention, it is provided that the features of the measurement signal (for example, the amplitude, frequency, and/or phase information) are determined in a specific time range after the application of a pulse of the stimulation signal, in particular in a time range of 10 ms to 100 ms, preferably 30 ms to 300 ms, after the application of a pulse of the stimulation signal.

Strong artifacts can occur at the measurement electrodes during the application of a pulse of the stimulation signal. These artifacts can be in the range of several volts, while the measurement signal to be derived, inter alia, is only in the order of magnitude of microvolts. In these cases, artifact suppression or filtering, inter alia, is not very promising and the signals measured during or immediately after the stimulation pulse are not taken into consideration in the calculation of the biomarker.

In other embodiments of the invention, all or at least some of the features of the measurement signal are continuously determined, i.e., without chronological restriction to a specific time window.

In a further embodiment of the invention, it is provided that a plurality of predefined stimulation sequences, in particular characterized by different amplitudes, frequencies, curve shapes, and location distribution, are successively applied and the biomarker is determined following each of them, and subsequently further stimulation is performed using the stimulation sequence with which the optimum value of the biomarker corresponding to the therapy goal is achieved.

This is a particularly simple method in this case, to select for a patient, from an array of known stimulation sequences, the stimulation sequence to which this patient responds best.

In a further embodiment of the invention, it is provided that the artificial noise comprises white noise and filtered noise (for example, f noise, 1/f noise, and/or $1/f^2$ noise), wherein switching is performed between various types of the artificial noise in dependence on the biomarker.

In a further embodiment of the invention, it is provided that first signals having a high proportion of noise, in particular a proportion of noise of greater than 10%, preferably greater than 50% in comparison to the carrier signal, and second signals having a low proportion of noise, in particular a proportion of noise of less than 10%, preferably less than 2% are generated and the first and second signals are applied in different regions of the patient and/or using different electrodes and/or coils.

The invention claimed is:

1. A noninvasive electrical and/or magnetic stimulation method for neuronal stimulation of a patient comprising the steps of:
deriving a measurement signal from at least one electrode in electrical communication with the patient,
generating a stimulation signal,
applying the stimulation signal by means of electrodes, i.e., electrical and/or magnetic stimulation,
determining a biomarker from the measurement signal, and
varying the stimulation signal in dependence on the biomarker,
wherein the biomarker is functionally dependent on the measurement signal, and wherein the method further comprises the step of:
determining the functional dependence of the biomarker by machine learning using training data from test subjects.

2. The method according to claim 1, wherein the measurement signal is an EEG signal.

3. The method according to claim 1, wherein the stimulation signal is an alternating current stimulation signal.

4. The method according to claim 1, wherein the stimulation signal comprises artificial noise.

5. The method according to claim 1, wherein the step of applying the stimulation signal by means of electrodes further comprises the sub-step of applying the stimulation signal in a region on or directly around the optic nerve of the patient.

6. The method according to claim 1, wherein the measurement signal includes items of frequency, amplitude, phase, and/or location information, and wherein the method further comprises the step of:
considering the frequency, amplitude, phase, and/or location information of the measurement signal when determining the biomarker.

7. The method according to claim 1, wherein the machine learning includes supervised clustering using support vector machines.

8. The method according to claim 1, wherein the method is for the treatment of vision disorders of the patient.

9. A noninvasive electrical and/or magnetic stimulation method for neuronal stimulation of a patient comprising the steps of:
deriving a measurement signal from at least one electrode in electrical communication with the patient,
generating a stimulation signal,
applying the stimulation signal by means of electrodes, i.e., electrical and/or magnetic stimulation,
determining a biomarker from the measurement signal, and
varying the stimulation signal in dependence on the biomarker,
wherein the method further comprises the step of: carrying out an optimization method during the stimulation to maximize the biomarker by way of a variation of parameters of the stimulation signal.

10. The method according to claim 9, wherein the measurement signal is an EEG signal.

11. The method according to claim 9, wherein the stimulation signal is an alternating current stimulation signal.

12. The method according to claim 9, wherein the stimulation signal comprises artificial noise.

13. The method according to claim 9, wherein the step of applying the stimulation signal by means of electrodes further comprises the sub-step of applying the stimulation signal in a region on or directly around the optic nerve of the patient.

14. The method according to claim 9, wherein the measurement signal includes items of frequency, amplitude, phase, and/or location information, and wherein the step of determining the biomarker further comprises the sub-step of:
considering the frequency, amplitude, phase, and/or location information of the measurement signal when determining the biomarker.

15. The method according to claim 9, wherein the optimization method is a stochastic optimization method.

16. The method according to claim 9, wherein the method is for the treatment of vision disorders of the patient.

17. A noninvasive electrical and/or magnetic stimulation method for neuronal stimulation of a patient comprising the steps of:

deriving a measurement signal from at least one electrode in electrical communication with the patient, the measurement signal including items of amplitude, frequency, and/or phase information,
generating a stimulation signal,
applying the stimulation signal by means of electrodes, i.e., electrical and/or magnetic stimulation,
determining a biomarker from the measurement signal, and
varying the stimulation signal in dependence on the biomarker,
wherein the method further comprises the step of:
ascertaining the amplitude, frequency, and/or phase information of the measurement signal in a specific time range after the application of a pulse of the stimulation signal.

18. The method according to claim 17, wherein the measurement signal is an EEG signal.

19. The method according to claim 17, wherein the stimulation signal is an alternating current stimulation signal.

20. The method according to claim 17, wherein the stimulation signal comprises artificial noise.

21. The method according to claim 17, wherein the step of applying the stimulation signal by means of electrodes further comprises the sub-step of applying the stimulation signal in a region on or directly around the optic nerve of the patient.

22. The method according to claim 17, wherein the measurement signal further includes location information, and wherein the method further comprises the step of:
considering the frequency, amplitude, phase, and/or location information of the measurement signal when determining the biomarker.

23. The method according to claim 17, wherein the specific time range is from 10 ms to 100 ms after the application of a pulse of the stimulation signal.

24. The method according to claim 17, wherein the specific time range is from 30 ms to 300 ms after the application of a pulse of the stimulation signal.

25. The method according to claim 17, wherein the method is for the treatment of vision disorders of the patient.

26. A noninvasive electrical and/or magnetic stimulation method for neuronal stimulation of a patient comprising the steps of:
deriving a measurement signal from at least one electrode in electrical communication with the patient,
generating a stimulation signal,
applying the stimulation signal by means of electrodes, i.e., electrical and/or magnetic stimulation,
determining a biomarker from the measurement signal, and
varying the stimulation signal in dependence on the biomarker,
wherein the method further comprises the steps of:
generating first signals having a high proportion of noise and
second signals having a low proportion of noise and
applying the first and second signals in different regions of the patient and/or using different electrodes.

27. The method according to claim 26, wherein the measurement signal is an EEG signal.

28. The method according to claim 26, wherein the stimulation signal is an alternating current stimulation signal.

29. The method according to claim 26, wherein the stimulation signal comprises artificial noise.

30. The method according to claim 26, wherein the step of applying the stimulation signal by means of electrodes further comprises the sub-step of applying the stimulation signal in a region on or directly around the optic nerve of the patient.

31. The method according to claim 26, wherein the measurement signal includes items of frequency, amplitude, phase, and/or location information, and wherein the method further comprises the step of:
considering the frequency, amplitude, phase, and/or location information of the measurement signal when determining the biomarker.

32. The method according to claim 26, wherein the proportion of noise of the first signals is greater than 10%.

33. The method according to claim 26, wherein the proportion of noise of the first signals is greater than 50%.

34. The method according to claim 26, wherein the proportion of noise of the second signals is less than 10%.

35. The method according to claim 26, wherein the proportion of noise of the second signals is less than 2%.

36. The method according to claim 26, wherein the method is for the treatment of vision disorders of the patient.

37. A noninvasive electrical and/or magnetic stimulation method for neuronal stimulation of a patient comprising the steps of:
deriving a measurement signal from at least one electrode in electrical communication with the patient,
generating a stimulation signal,
applying the stimulation signal by means of electrodes, i.e., electrical and/or magnetic stimulation, wherein the applying step includes the step of successively applying as the stimulation signal a plurality of predefined stimulation sequences,
determining a biomarker from the measurement signal following each application of the plurality of predefined stimulation sequences,
varying the stimulation signal in dependence on the biomarker,
carrying out an optimization method during the stimulation, the optimization method providing an optimal value of the biomarker, and
subsequently performing further stimulation using the stimulation sequence with which the optimum value of the biomarker was achieved.

38. The method according to claim 37, wherein the measurement signal is an EEG signal.

39. The method according to claim 37, wherein the stimulation signal is an alternating current stimulation signal.

40. The method according to claim 37, wherein the stimulation signal comprises artificial noise.

41. The method according to claim 37, wherein the step of applying the stimulation signal by means of electrodes further comprises the sub-step of applying the stimulation signal in a region on or directly around the optic nerve of the patient.

42. The method according to claim 37, wherein the measurement signal includes items of frequency, amplitude, phase, and/or location information, and wherein the method further comprises the step of:
considering the items of frequency, amplitude, phase, and/or location information of the measurement signal when determining the biomarker.

43. The method according to claim 37, wherein the method further comprises the step of:
distinguishing the plurality of predefined stimulation sequences by different stimulation parameters, the different stimulation parameters including at least one of amplitudes, frequencies, curve shapes, and location distributions.

44. The method according to claim 37, wherein the method is for the treatment of vision disorders of the patient.

* * * * *